United States Patent [19]

Delao

[11] Patent Number: 5,592,953
[45] Date of Patent: Jan. 14, 1997

[54] TUBULAR SLEEVE WITH ELASTICIZED SEALING MEANS

[76] Inventor: Wenda K. Delao, 1517 S. 7th St., La Crosse, Wis. 54601

[21] Appl. No.: 627,682

[22] Filed: Apr. 2, 1996

[51] Int. Cl.⁶ ................................................ A61F 5/37
[52] U.S. Cl. ................................. 128/882; 602/3
[58] Field of Search ....................... 128/846, 877, 128/878, 879, DIG. 18, DIG. 15, 856; 602/3, 8; 2/2, 22, 16, 59, 240

[56] References Cited

U.S. PATENT DOCUMENTS

| | | | |
|---|---|---|---|
| 2,169,203 | 8/1939 | Hinchliff | 66/178 |
| 2,704,069 | 3/1955 | Donelan | 128/881 |
| 4,016,027 | 4/1977 | Kintanar | 2/159 |
| 4,133,624 | 1/1979 | Heavner et al. | 425/275 |
| 4,287,608 | 9/1981 | Meyer | 2/16 |
| 4,315,504 | 2/1982 | Drennan | 128/881 |
| 4,646,727 | 3/1987 | Chambers | 128/882 |
| 4,856,112 | 8/1989 | Effle | 2/59 |
| 4,926,851 | 5/1990 | Bulley | 128/157 |
| 4,971,233 | 11/1990 | Keenan | 223/111 |
| 4,991,593 | 2/1991 | LeVahn | 128/856 |
| 5,016,648 | 5/1991 | Brown | 128/879 |
| 5,063,919 | 11/1991 | Silverberg | 602/3 |
| 5,187,813 | 2/1993 | Klein | 2/16 |
| 5,357,633 | 10/1994 | Rael | 2/16 |

*Primary Examiner*—Michael A. Brown
*Attorney, Agent, or Firm*—M. Paul Hendrickson

[57] ABSTRACT

The invention provides protective sleeves for protectively covering an appendage and medicinal sites such as intravenous equipment, bandages, wounds, etc. The sleeve is open at both ends with adjustable elastic sections which effectively seal the sleeve against the appendage. The elastic sections are equipped with elastic drawstrings which circumscribe a cushioning resilient layer. When the drawstrings are drawn and tied together the elastic force of the drawstring applies a sealing force to the resilient layer causing the layer to conform to the appendage configuration and seal the elastic section against the appendage. The wearer of the protective sleeve may safely shower and protect the medicinal site from contamination. When finished showering, the drawstrings may be untied to release the contractive force so as to permit the sleeve to be removed from the appendage.

20 Claims, 3 Drawing Sheets

TUBULAR SLEEVE WITH ELASTICIZED SEALING MEANS

FIELD OF THE INVENTION

This invention relates to a bloused, water-repelling protective sleeve, open at both sleeve ends tier slipping the sleeve over a bodily appendage and a medicinal site, and equipped to protectively seal the medicinal site from water and environmental contamination, and its manufacture and use.

BACKGROUND OF THE INVENTION

Conventional medicinal practice for protecting a medicinal site (e.g. intravenous sites, bandages, compresses, wounds, topical medicinals) of an appendage of a hospitalized or institutionalized patient when showering or bathing is to wrap and tape a plastic wrap about the medicinal site and appendage. Sealing of the medicinal site from external contamination and damage is often unsuccessful. Taping of the plastic wrap to cover the medicinal site generally requires taping the plastic wrap to the appendage. The taped seal occasionally fails to adhesively adhere to the appendage allowing water and other contaminants to damage or contaminate the medicinal site. Consequently, considerable time and effort to reestablish a damaged or contaminated medicinal site is often required by medical personnel. The taped plastic wrap is also generally bulky and uncomfortable. Removal of the taped plastic can result in pain or injury to the patient or the medicinal site.

The prior art generally reflects an unawareness of an oversized tubular, water-repelling sleeve protector that is open at both ends for slipping over an appendage, and equipped at both tubular ends with cushioned, elasticized means for drawing the sealing ends snugly against the appendage to internally seal the medicinal site from water and other environmental contamination. Also undisclosed is a method for manufacturing and using such sleeve to protect a medicinal site or an appendage from exposure by pulling a tubular sleeve with elasticized means over the human appendage.

Illustrative of the prior art teachings are the following patents:

U.S. Pat. No. 4,971,233 discloses a sterile glove which, when removed from a package in which it is contained, is pulled generally in the direction of unrolling, and a tab or string unrolls the glove along the wearers forearm.

A cosmetic glove having a hand and arm-receiving portion that is connected by overlapping straps provided on the back of arm-receiving portions is disclosed in U.S. Pat. No. 4,016,027.

U.S. Pat. No. 4,926,851 discloses tubular bandages in rolled form with one end portion rolled outwardly from the free end of the bandage and the other end portion rolled inwardly from the opposite free end, so that in use, a bandage of suitable size may be selected and easily fitted around a body part to be bandaged.

There exists a need for a protective sleeve which may be utilized for a wide variety of different sized and shaped appendages in protecting a medicinal site from contamination and damage. A protective sleeve which could be readily applied to the medicinal site and sanitarily sealed against external contaminants would fulfill a long existing health care need. Protective sleeves which could easily be applied, removed and reused without creating discomfort or injury to the patient would represent a substantial advance and savings in costs and labor for providers of health care services.

SUMMARY OF THE INVENTION

One objective of the invention is to provide an oversized tubular, water-repelling sleeve protector that is open at both ends for slippage over a human appendage to protect a medicinal site from external exposure, wherein the protector is equipped at both tubular ends with elasticized means for drawing the ends snugly against the appendage to internally seal a protectively covered medicinal site such as intravenous sites, surgical bandages, compresses, sauves, topical ointments, medicinal applications, wounds, etc. from environmental contamination such as occurs when bathing, showering, etc.

A further objective of the invention is to provide a method of protecting a human appendage from external contamination by pulling an oversized tubular, water-protecting sleeve protector that is open at both ends over the appendage; wherein the protector is equipped at both tubular ends with elasticized cushioned means to protect the appendage from external exposure.

Another objective of the invention is to provide for the manufacture of a protective sleeve for use in protecting a medicinal site from contamination.

The foregoing and other objects of the invention are generally accomplished by providing an elongated sleeve that fits over a body portion such as an appendage (e.g. forearm, elbow and/or upper arm, ankle, knee, thigh, calf, etc.) and which is equipped with a plurality of elastic bands circumferentially disposed in a lateral spaced relationship, and openings for said elastic bands through which elastic bands are threaded in order to permit an application of a uniform pressure to the appendage. The application of a uniform and cushioned pressure by the elastic bands may be effectively accomplished by a foam rubber layer disposed between the band and the appendage which cushions the compressive force of a stretched elastic band. The foam rubber layer in cooperative association with encircling elasticity of the band against the appendage allows the sleeve to conform to any appendage size and effectively seal the internal confines (i.e. sleeve chamber) from external exposure while preventing a tourniquet effect and also increasing patient comfort by a cushioning of the sealing force.

DETAILED DESCRIPTION OF THE INVENTION

Figure 1:
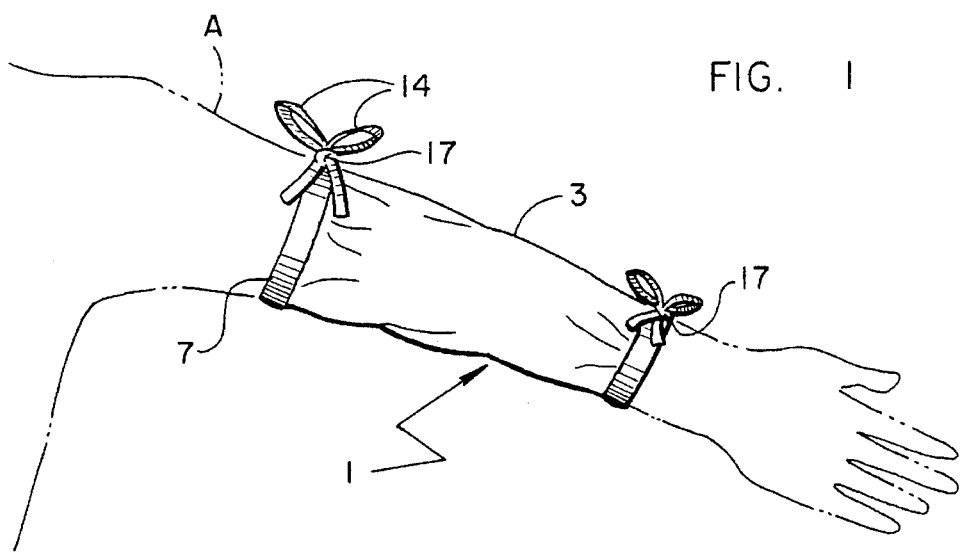
FIG. 1 depicts a partial view of a human body fitted with a protective elongated sleeve of this invention emplaced over a portion of a patient's arm with the elastic sections of the sleeve equipped with elastic straps shown as being tightened and securely tied so as to apply a uniform sealing pressure about the arm.

With reference to the FIGS. 1–6, there is provided a protective sleeve (generally designated as 1) useful for placement over a bodily appendage A such as an arm A to protect a medicinal site S (illustrated in FIG. 3 and otherwise hidden from view beneath sleeve 1) from external contamination, said sleeve 1 comprising an elongated water-resistant sleeve member 3 housing an internally disposed sleeve chamber 5 for protectively covering the site S, a plurality of laterally disposed elastic sections (generally designated as 10) for sealing the sleeve member 3 against the appendage A, with each of said elastic sections 10 including a resilient layer 12 circumscribing an internally disposed sleeve opening 7 which provide an open passageway for slipping the sleeve member 3 over the appendage A, and an elastic band 14 circumferentially disposed about the resilient layer 12 so that the band 14, when elastically drawn, applies a uniform compressive force against layer 12 to protectively seal sleeve member 3 against the appendage A.

The body of sleeve 1 is fabricated from a water-propellant sleeve member 3 which protects the patient's medicinal paraphernalia harbored within the protective sleeve 1 from wetting and contamination during bathing or showering. As may be observed from the figures, the sleeve 1 includes drawing means 14 (depicted as drawstrings 14) which allow sleeve member 3 to be compressively drawn against the appendage A and thereby seal sleeve openings 7 at both ends of protective sleeve 1. A water-tight seal between the appendage A and the protective sleeve 1 arises through a combination of the elastic drawstring's 14 ability to adjust to different circumferential diameters and the resilient layer's 12 ability to compressively contour to the size and shape of appendage A.

In the preferred embodiments of the invention as depicted in the figures, sleeve 1 defines an internally disposed sleeve chamber 5 terminating by sleeve openings 7 (at each sleeve 1 end) equipped with variably adjustable elastic sections 10 which may be suitably adjusted so as to apply the appropriate elasticity for sealing sleeve 1 to different sized and shaped appendages A. The protective sleeve 1 is designed to fit over different sized arms A and eliminate a current practice of using plastic wraps wound about the medicinal site and taped to the patient's appendage A. Adjustability of the elastic sections 10 may be conveniently accomplished by a pair of drawstrings 14 oppositely positioned at sleeve ends of sleeve 1 so as permit the sleeve member 3 to be snugly drawn onto the appendage A. The elastic drawstring 14 may be constructed of any suitable elastic material which is capable of applying a compressive force against the resilient layer 12. Natural and synthetic rubber possessing sufficient elasticity to apply a uniform retractive force (i.e. contraction) against the resilient layer 12 may be used for this purpose. Elastic drawstrings 14 fabricated from flat elastic stock such as conventionally used in the clothing industry may be effectively utilized for this purpose.

Figure 2:
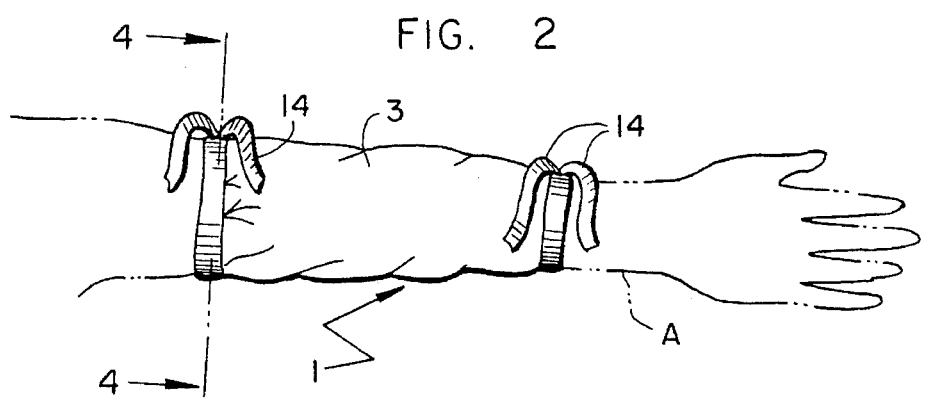
FIG. 2 is another view showing the protective elongated sleeve shown in FIG. 1 emplaced over the arm with the elastic sections being drawn tautly about the arm but untied.

Referring more particularly to figures, there is shown a protective elongated sleeve 1 having elasticized sections 10 margining onto sleeve openings 7 at opposite sleeve ends which are adjustable to fit different arm sizes and capable of being eased over intravenous or other medicinal sites. The sleeve 1 enables the wearer to comfortably shower or bathe and yet maintain dryness and sepsis of the intravenous site S or other medicinal site S (such as a surgical dressing as depicted by the cross-sectional view of FIG. 3 ) applied to a wound or injury which is protectively covered by the protective sleeve 1. The protective sleeve 1 is preferably sized so as to universally fit to a broad range of different sized appendages A at various locations or sites throughout the entire appendage length. In its normal use, the protective sleeve 1 is typically designed so as to partially fit over appendage A (e.g. forearm, upper arm and/or elbow such as depicted by FIGS. 1 and 2) and when the elastic sections 10 are drawn securely about the appendage A to a contracted position as shown in FIG. 1, sleeve 1 protectively covers and seals the medicinal site S from external contamination. Circumferential ports 15 laterally disposed in the elastic sections 10 provide portals from which the two loose ends of drawstring 14 protrude. This arrangement provides an adjustable drawing means for drawing drawstrings 14 through the ports 15. This provides for adjustably stretching and applying an appropriate level of tension and compressive force against layer 12 so as to effectively seal sleeve member 3 against intrusion of water into chamber 5. Upon achieving the desired tension upon drawstrings 14, the invention provides, in general, securing means 17 wherein loose ends may be tied or secured together as shown in FIG. 1. Drawstring 14, in cooperative association with resilient layer 12, protectively seals the water-repellent sleeve member 3 against any desired section of appendage A while also permitting an appropriate uniform pressure to be applied and distributed thereby so as to match and effectively seal any arm A size at sleeve openings 7.

Figure 3:
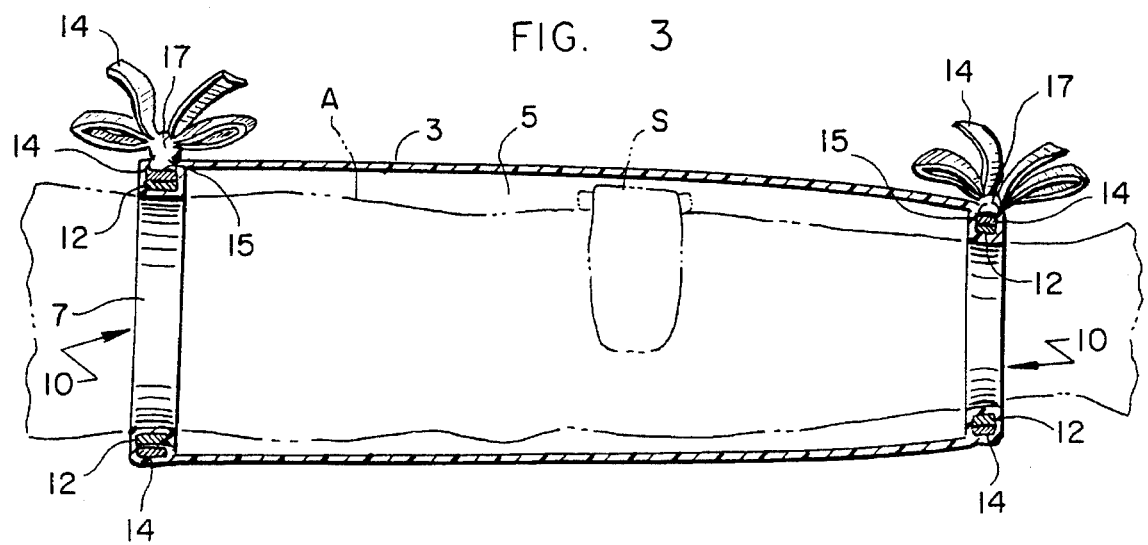
FIG. 3 is a cross-sectional view taken along lines 3—3 of FIG. 2 and showing a medicinal site protectively covered by the sleeve.
Figure 4:
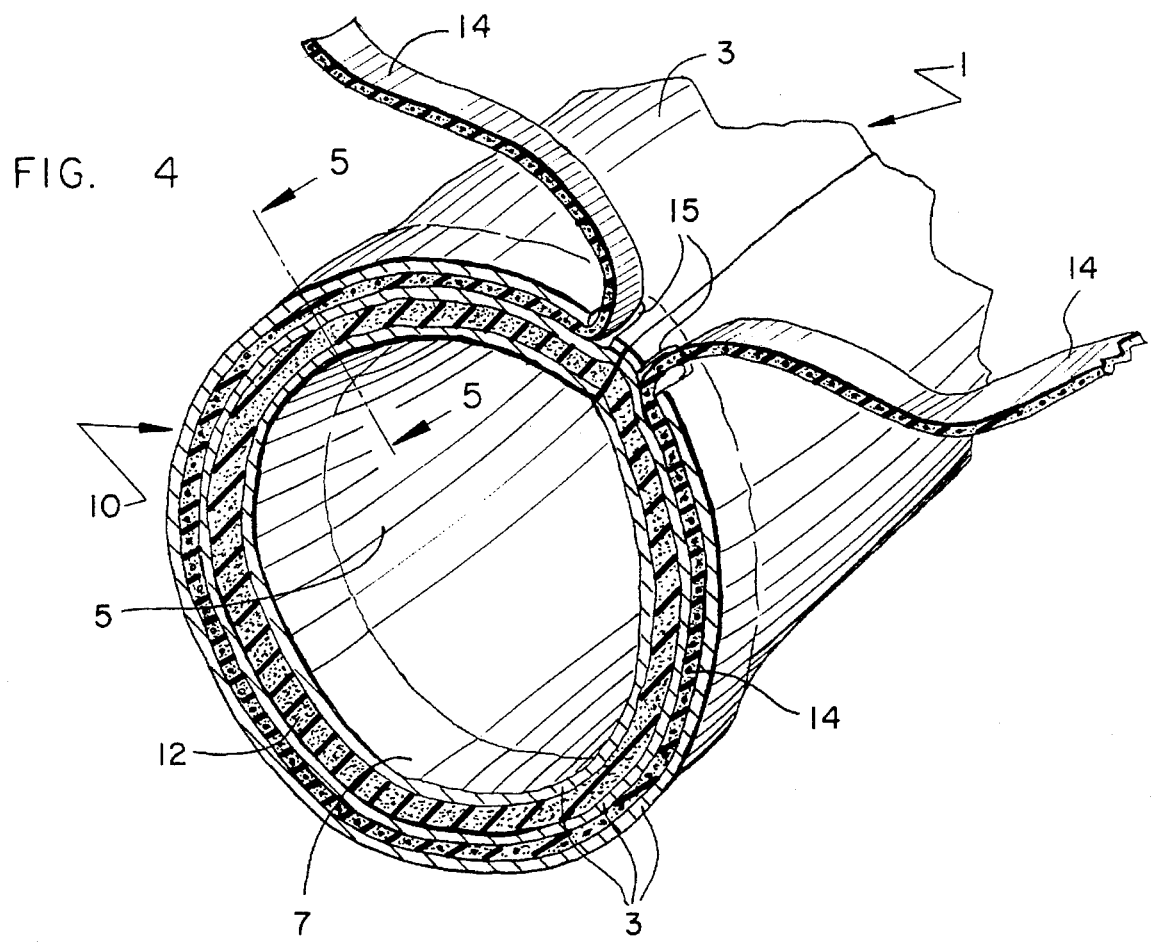
FIG. 4 is perspective cross-sectional view taken along line 4—4 of FIG. 2 detailing in greater detail the elastic section of a sleeve end.

FIGS. 2 and 4 depict the water-repellent protective sleeve 1 with untied drawstring 14 ends extending through and from circumferential ports 15 of elastic sections 10. As may be observed from the cross-sectional views of FIGS. 3–5, drawstrings 14 circumscribe about a thin layer of a resilient layer 12 which is advantageously a porous resilient material and preferably a foam rubber layer 12. When drawstrings 14 are stretched and tied while maintaining the drawstrings under tension at a contracted position as shown in FIGS. 1 and 3, the drawstrings 14 will apply a uniform elastic pressure of sufficient compressive force so as to form an effective seal onto the sleeve member 3 interfacing onto appendage A without interfering with normal blood circulation or other internal body functions. The sealing efficacy of the elastic sections 10 permits showering or bathing while maintaining sepsis of the intravenous or IV sites as well as keeping any dressing or bandage (e.g. wounds or injuries) applied to the medicinal sites dry. In the preferred embodiments of the invention, the drawing means 14 is designed so as to apply a substantially uniform compressive force upon resilient layer 12 and the sleeve member 3 interfacing onto appendage A so as to effectively form a protective seal therebetween. When drawstrings 14 are permitted to freely circumferentially move and to be uniformly drawn about resilient layer 12, a higher degree of uniformity in compressive force and sealing efficacy can be accomplished at elastic section 10. By interdisposing an interfacing sleeve member 3 of a low coefficient of friction (such as common with most thermoplastic films) between the drawstring 14 and resilient foam layer 12 as illustrated by the cross-sectional views, drawstrings 14 will move freely and may be drawn uniformly about resilient layer 12 so as to apply a uniform, non-tourniqueting seal against appendage A.

The protective sleeve 1 includes a water-resistant external sleeve member 3 which, in cooperative association with the elastic sections 10, effectively shields internal sleeve chamber 5 of sleeve 1 from external contamination when the sleeve 1 is protectively placed and sealed over an appendage A. The sleeve member 3 also serves as a protective aseptic covering for the sleeve components against contamination and provides a smooth external surface which may be more easily cleaned and sterilized. Since elastic sections 10 permit sleeve 1 to be variably adjusted to fit different appendage sizes, sufficient sleeve chamber space 5 should be allotted by sleeve member 3 so as to accommodate for various arm sizes and medicinal site S. Accordingly, the cross-sectional size of the protective sleeve 1 is preferably oversized in relation to the circumferential appendage size so as to provide sufficient sleeve chamber 5 space to accommodate both appendage A and the medicinal accessories of the medicinal site S. Oversizing of protective sleeve member 3 results in a bloused sleeve 1 typically of a cross-sectional size (diameter at bicep of arm) of a least 125 percent greater in size than appendage size and more typically at least 150 percent greater in diameter than the customary appendage size. Oversizing by blousing sleeve 1 to a cross-sectional diameter by a factor of two fold or more from normal appendage bicep size may be adapted to the sleeve 1 but is generally unnecessary. Sleeve openings 7 should, however, be sized so as to fit substantially snuggly against appendage A without any substantial overlapping of sleeve member 3 when drawstrings 14 are drawn to a contracted protective sealing position. The sleeve 1 length will depend primarily upon the particular appendage A which the sleeve 1 is intended to be used as a protective sleeve 1. Infants and smaller children have smaller arm and legs than adults and, accordingly, protective sleeves 1 for children would be smaller in circumferential size and length than adults. Similarly, the drawstring 14 elasticity for an infant or child would be of type adapted to apply less tension and contracting forces (e.g. to prevent a tourniquet effect) than drawstrings 14 :for adult sleeves 1. Infant protective sleeves 1 may measure as little as one or more inches in circumference and two inches in length, whereas adult-sized protective sleeves 1 may measure a foot or more in length and a foot or more in circumferential size for certain oversized uses. As mentioned, the circumferential size (i.e. internal chamber size) at the sleeve openings 7 should be tailored so as to avoid overlapping of the elastic sections 10 when drawstrings 14 are drawn tautly about the appendage A. The circumference of upper arm and lower forearm sizes of sleeves 1 for adult males can vary considerably. Arm sizes for adult male arms will typically range from about six to about nine inches in circumference at the wrist and about 15 to about 25 inches in length from wrist to armpit. The upper arm and forearm sizes will typically range from about 1½ to about 2½ times greater in circumferential sizes than the typical wrist circumferential size. Protective sleeves 1 designed to protect medicinal sites S at an adult leg (not shown) would also be correspondingly larger in size than protective arm sleeves and may, likewise, be equipped with wider and thicker drawstrings 14 so as to apply the appropriate sealing pressure against a somewhat larger sized resilient layer 12. The length of the protective sleeve 1 for arm use will typically accommodate from about ¼ to about ½ of the full arm length when used for protecting arm sites and most usually range from about six inches to about 12 inches in length. Three different sizes of protective arm sleeves 1 may be generally adopted to universally cover most uses for children and adults.

The sleeve member 3 may be constructed of a wide variety of flexible waterproof or water-resistant materials such as commonly used in the manufacture of protective rain wear and garments. Any flexible waterproof or water-resistant material, such as thermoplastics films, natural and synthetic fabrics possessing a water-repellent surface and the like, may be used in fabricating the sleeve members 3 of this invention. Natural occurring materials (e.g. canvas, silk, rubber, natural fabrics coated with a water-repellent surface, etc. preferably of a low coefficient of elasticity) and synthetic materials such as polymeric materials (e.g. thermoplastics such as polyethylene, polypropylene, rayon, dacron, nylon, polyvinyls, polystyrenes, acrylates, acrylonitriles, etc.) possessing the necessary flexibility, durability and water-resistance may be utilized to fabricate sleeve member 3. The sleeve member 3 may be alternatively constructed of an elastic material possessing sufficient elasticity to protect the medicinal site S without creating a tourniquet effect. Thermoplastic film and sheet stocks (e.g. 0.5 mm–10 mm thickness) provide a particularly effective and inexpensive raw material source for fabricating the sleeve member 3 of this invention.

The protective sleeve 1 is suitably provided as a tubular sleeve with sleeve openings 5 at both sleeve ends which permit sleeve 1 to be easily placed upon appendage A. The depicted sleeve 1 includes two elastic sections 10 at the opposite sleeve ends for adjustably fitting the sleeve 1 to meet a diverse size range of appendages A and to allow the sleeve 1 to be effectively drawn over the appendage A without disrupting paraphernalia at the medicinal site S. The tubular protective sleeve 1 is equipped with elasticized sealing means 10 designed to protect but not necessarily form a watertight seal against the intrusion of water such as may arise from total immersion. The elastic sections 10 in the preferred embodiments of the invention include adjustable drawing means 14 so as to allow the elastic sections 10 to be adjusted to any appendage size. By providing the elastic member as adjustable drawing means 14 such as may be accomplished by the protruding ends of drawstrings 14 extending from ports 15 as illustrated in the Figures, the elastic sections 10 at both sleeve openings 15 may be appropriately adjusted so as to accommodate and apply the appropriate elasticity for sealing the sleeve opening 7 against the appendage A without creating discomfort or a tourniquet effect. The drawstrings 14 are preferably of an elastic construction and loose at both ends so that when they are drawn through ports 15, drawstrings 14 will apply sufficient contractive and compressive forces to seal sleeve 1 against appendage A without adversely affecting body functions and blood circulation. Although an elastic member 14 stretched to an appropriate elasticity may be sewn or anchored to the sleeve 1, the elastic member 14 is preferably of an adjustable drawstring type as depicted by the Figures which effectively accommodates different sized appendages A as well as permitting different positioning of the sleeve 1 upon the appendage A.

The elastic drawstrings 14 are of a size and elasticity so as to apply sufficient elastic force for sealing the sleeve 1 to the appendage A without creating a tourniquet effect upon the user. The elasticity of drawstring 14 will depend largely upon its composite structure and size. Elastic drawstring 14 of the flat band type (e.g. braided elastic type) generally apply a more uniform contractive pressure upon resilient layer 12 than the rounded type and, thus, are preferably utilized as drawstrings 14 herein. Elastic bands 14 such commonly used by tailors and seamstresses as elastic arm or sleeve bands are particularly useful as drawstrings 14 herein. Such elastic bands 14 may be suitably fabricated from braided rubber (e.g. 16%) and polyester (e.g. 84%) fibers. Illustrative braided elastic bands for use may measure from about ⅛ inch width up to about an inch or more in width with the wider braided elastic bands being generally more useful for use as protective arm sleeves 1 for mature adults and in protective leg sleeves 1 use. The smaller braided elastic widths generally possess less contractive forces and, therefore, are less likely to create a tourniquet effect in protective sleeves 1 for small children than the wider braided elastic bands. Braided elastic bands measuring from about 10 to about 20 centimeters in width are generally useful for drawstrings 14 in protective arm sleeves 1 herein. The amount or level of applied tension may also be generally controlled by the extent by drawstring 14 is stretched to the desired contractive position.

The drawstrings 14 generally circumscribe a foamed rubber layer 12 preferably with an interfacing sleeve member 3 interdisposed between the drawstrings 14 and foamed layer 12 which allows the drawstring 14 to freely move and uniformly compresses the foamed rubber layer 12 and sleeve member 3 against the appendage A.

In the preferred embodiments of the invention, an effective water seal at each sleeve opening 7 relies upon the elasticized drawstring 14 band separately encased within a drawstring channel casing 16 equipped with entry and exit ports 15 so as to allow the threaded elasticized drawstring 14 to move freely about layer 12 and enable said drawstring 14 to be securely tied in a secured position as shown in FIGS. 1 and 3. The drawstring channel 16 containing the elasticized band 14 preferably circumscribes resilient material layer 12 of a slightly wider size in width size than band 14 so as to permit a more uniform distribution of the sealing force against the interfacing sleeve member 3 and appendage A. The resilient layer 12 is also preferably separately sealed and encased within resilient layer channeled encasement 18. The resilient material 12 provides a cushion for the elastic band 14 and functions as a distributor for uniformly distributing the elastic force of band 14. The cushioning effect significantly aids in allowing the sleeve 1 to conform to the wearer's appendage A and provide a "custom fit" for each wearer. The combination of elasticized drawstring 14 circumscribing the resilient porous material 12 facilitates effective adjustment of the elastic section 10 to conformingly seal against various portions of the appendage A as well as various sized appendages. Sealing the porous material 12 within the sleeve member 3 and beneath the elastic drawstring 14 maintains dryness and aseptically shields the resilient material 12 from undesirable microbiological contamination so as to permit drip-drying and reuse of the sleeve 1.

The resilient layer 12 may be constructed of a variety of resilient material which cushion the contractive pressure against sleeve member 3 and prevent the stretched elastic drawstring 14 from applying an excessive contractive force upon the appendage A. The resilient material 12, in cooperative association with the drawn drawstring 14, effectively distributes the contractive force and exerts a uniform compressive force about the appendage A so as to protectively seal the sleeve member 3 against the appendage A and prevent externally applied moisture (e.g. such as shower or bath water) from seepage within the internal confines of the sleeve chamber 5. Illustrative resilient material for the resilient layer 12 include natural and synthetic rubber, especially foamed rubber (closed or open cellular foam structure), cloth and felt, etc. A soft foam rubber layer 12 of a natural or synthetic origin (closed or open cellular structure) has been found particularly effective for use in fabricating the resilient layer 12. Such foam rubber layers 12 inherently possess a resilient structure which, when placed under tension by drawstrings 14, will uniformly distribute the compressive forces throughout layer 12 which, in turn, uniformly radiates the sealing effect of sleeve member 3 against appendage A. Relatively thin layers of foam rubber (e.g. about one to about ten mm thickness) are generally used in uniformly distributing and exerting an effective sealing force upon sleeve member 3. The resilient layer 12 will preferably be wider in width than the drawstring 14 width and will range for most uses from about two to about five mm or more in thickness. A closed cell foamed rubber is preferable since it is less prone to microbiological contamination.

The sleeve suitably includes securing means 17, as illustrated by FIGS. 1 and 3, for securing and maintaining the elastic means 14 at a contractive position when drawn to a contractive position. The securing means 17 in the case of depicted drawstrings 14 involves securely fastening drawn sections of drawstring 14 together. Such a securing means 17 may be simply accomplished by threading a sufficient length of the opposing drawstring 14 ends through drawstring ports 15 to permit drawstring 14, when elastically drawn to the contractive position, to be tied together as illustrated in FIG. 1. If desired, more complicated securing means 17 (not shown) such as buckles, snap buttons, clasps, pressure sensitive fasteners, etc. may be utilized for fastening the drawstrings 14 or other elastic means at a desired contractive position.

Most resilient materials typically used in fabricating the resilient layer 12 possess a relatively high coefficient of friction which provides a highly tractive interface for the elastic drawstring 14 which, in turn, can interfere with the uniformity of tension along the entire drawstring length and may result in non-uniformity of drawstring compressive pressure applied to the resilient layer 12. Inserting an interfacing separator at the drawstring 14 interface with layer 12 allowing drawstring 14 to freely move about layer 12. By utilizing the sleeve member 3 as a slip separator or separating membrane between the elastic drawstring 14 and the resilient layer 12, drawstring 14 when stretched and contracted, will thus freely move about the separating membrane 3 interface and about the layer 12 which in turn permits drawn drawstring 14 to uniformly stretch and apply a uniform compressive pressure against the resilient layer 12 and the sleeve member 3. This results in more effective sealing of sleeve member 3 against appendage A. In general, most water-resistant stock materials fabricated from thermoplastics for use in the manufacture of the sleeve member 3 will typically provide a low coefficient of friction (i.e. a relatively slippery interface) so as to allow the drawstring 14 to freely circumferentially move about the resilient layer 12. If materials of a relatively high coefficient of friction (e.g. such as natural and synthetic rubber) are used to make the sleeve member 3, an intervening layer (not shown) of a low coefficient of friction may be appropriately placed over or affixed to the resilient layer 12 so as to permit the drawstring 14 to freely move about the resilient layer 12.

Drawings 1–5 illustrate the preferred cooperative combination of the working components of elastic sections 10. The elasticized drawstring 14 is preferably separately encased within an outer channel casing 16 of sleeve member 3 which serves as a housing for drawstring 14. The porous resilient layer 12 is also preferably separately encased within an inner channel casing 18 by sleeve member 3, which places layer 12 at a fixed circumferential position. This arrangement allows the elasticized drawstring 14 to freely slide at the desired degree of tautness about the appendage A while allowing the resilient layer 12 to further enhance the ability of sleeve member 3 to effectively seal at each sleeve opening 7 of the sleeve 1 by contouringly conforming and cushioning the sleeve member 3 about the entire interfacing circumference of the appendage A. This unique combination provides a snug, comfortable, watertight fit without creating a tourniquet effect. The cooperative combination also contributes to the ease of removing the protective sleeve 1 by simply unsecuring the securing means 17 of drawstring 14 (e.g. by untieing) and slipping the sleeve 1 from appendage A.

Figure 6:
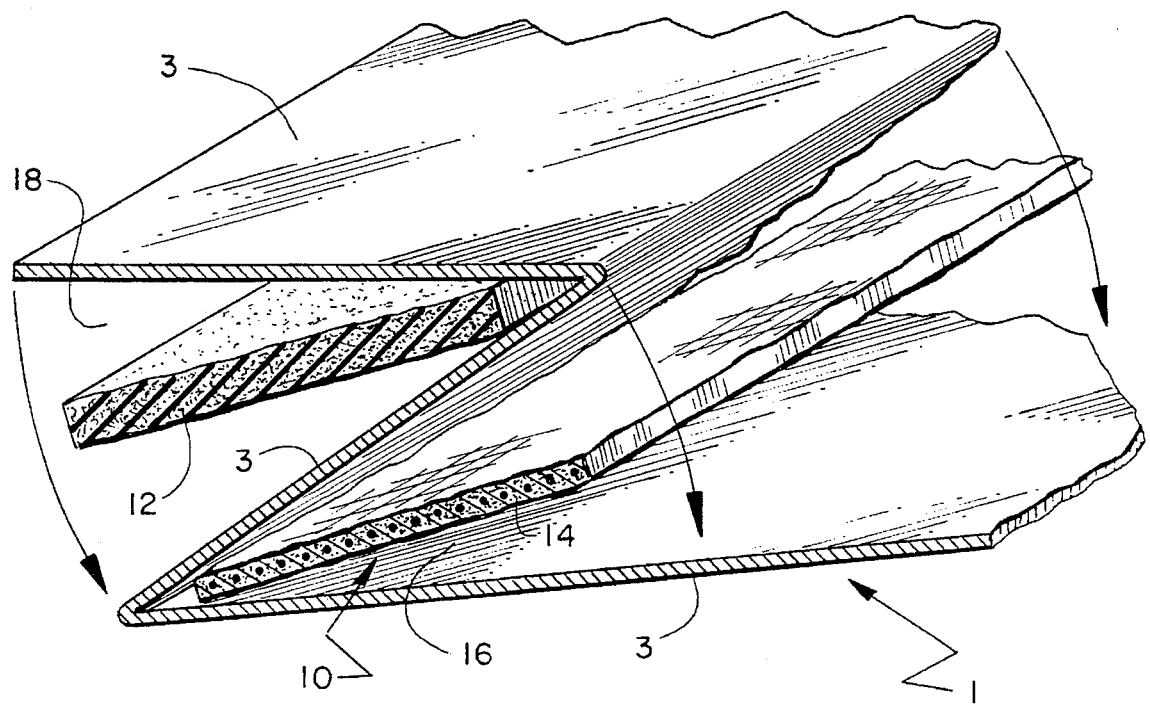
FIG. 6 is a partial view of an unfabricated sleeve end of a sleeve member and which view S depicts its use in fabricating the elastic sections of the sleeve.

The present invention also provides a method for manufacturing a protective sleeve 1 useful for placement over a bodily appendage A to protect a medicinal site S from external contamination wherein the sleeve 1 includes an elongated water-resistant sleeve member 3 for covering site S, a plurality of laterally disposed elastic sections 10 for sealing the sleeve member 3 against the appendage A and the medicinal site S from the external contamination, with each of said elastic sections 10 including a resilient layer 12 circumscribing an internally disposed sleeve opening 7 disposed at each sleeve end for slipping the sleeve member 3 over the appendage A, an elastic drawstring 14 circumferentially disposed about the resilient layer 12 so that the drawstring 14, when elastically drawn, applies a compressive elastic force against the layer 12 to protectively seal the sleeve member 3 against the appendage A, with said drawstring 14 and said resilient layer 12 being separately encased within said sleeve member 3, said method comprising:

a) patterning the sleeve member 3 from a sheet of a water resistant material;

b) bifolding the sleeve member 3 at the sleeve opening 7 at each sleeve end to provide accordion-shaped pleated folds (as depicted by FIG. 6) having an outer pleated channel 16 for receiving the drawstring 14 therewithin and an inner pleated channel 18 for housing the resilient layer 12 therewithin;

c) inserting the drawstring 14 within the outer channel 16 and the resilient layer 12 within the inner channel 18; and d) separately encasing said drawstring 14 within said outer channel 16 and said resilient layer 12 within said inner channel 18.

In the preferred embodiments of the invention as illustrated in the figures, sleeve member 3 is effectively utilized to form inner channel casing 18 and the outer channel casing 16. By so providing separate channeled housing, drawstring 14 and resilient layer 12 may be maintained in a proper positioning and relationship for cooperative interrelationship within elastic sections 10 which results in more effective sealing of the sleeve member 3 about the appendage A at both chamber openings 7. As previously mentioned, the separate encasement of both the drawstring 14 and resilient layer 12 utilizing the sleeve member 3 as a separating layer therebetween allows the drawstring 14 to move freely about the resilient layer 12 and apply a constant circumferential and uniform sealing pressure against resilient layer 12.

Pursuant to the preferred embodiments for manufacturing the protective sleeve 1, the sleeve member 3 is cut from a flat sheet stock of water-resistant material to a size sufficient to circumscribe the appendage A and the medicinal site S leaving additional margining edges along both sleeve openings 7 to provide sufficient sleeve member 3 an arterial for forming the accordion-pleated bifolds for the outer channel casing 16 for housing drawstring 14 and the inner channel casing 18 for housing resilient layer 12. The oversizing in width of sleeve member 3 results in a bloused sleeve 1 which may be easily drawn over the appendage A without disrupting medical paraphernalia (e.g. IVs) at the medicinal site S.

Additional sleeve member 3 material should also be provided along longitudinal sleeve axis for seaming the margining edges of sleeve member 3 together to form tubular sleeve and its chamber 5. The pattern or template for cutting sleeve member 3 from the water-resistant sheet stock is accordingly oversized in relation to the appendage size so as to accommodate for the protruding paraphernalia at the medicinal site S as well as providing additional sleeve member 3 material in forming the encasements 16 and 18 for the drawstrings 14 and resilient layer 12 at both sleeve ends 7 and to permit the seaming together of the flat sheet stock to form tubular sleeve 1.

Figure 5:
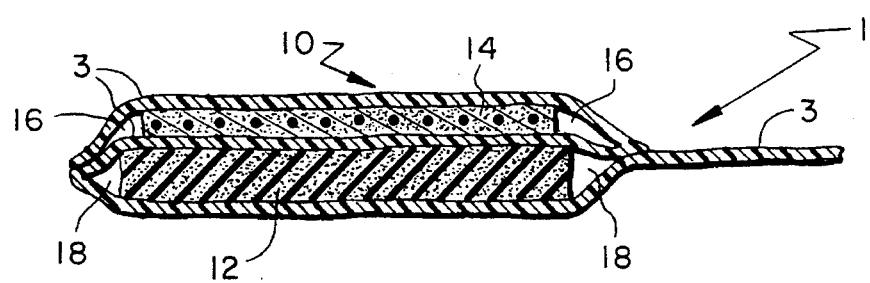
FIG. 5 depicts an enlarged and partial cross-sectional view of the elastic section taken along line 5—5 of FIG. 2.

Separate casings (16 and 18) for drawstring 14 and resilient layer 12 may be effectively fabricated from flat stock at both sleeve openings 7 of the sleeve member 3 by creating a pleated accordion bifold by a bifolding technique as depicted by FIG. 6. This bifolding technique, as shown, involves folding a bordering end margin at each end of sleeve opening 7 to 360 degrees (i.e. folding stock bordering margin onto itself) with the initial fold providing an end margin fold sufficient for casings 16 and 18 (i.e. both encasements) and then by reverse bifolding a bisectional portion of the initial fold to form an accordion-pleated bifold or a Z-shaped bifold configuration at each end of the sleeve appendage openings 7 (as depicted by FIG. 6) to which the drawstring 14 and resilient layer 12 may be inserted. In the manufacture, two exiting slits or ports 15 for each of the drawstrings 14 are made within each of the elastic sections 10 at a position which ultimately becomes the outer surface of sleeve member 3. Terminal end portions of the drawstrings 14 are threaded through the ports 15 to provide the securing means 17 with the balance of the unstretched drawstring 14 being placed flushly within the accordion-pleated bifold of what is shown as the outer channel casing 16 as depicted by FIGS. 3–5. In practicing the actual manufacture, the resilient layer 12 is placed within the lower Z channel or external channel of the bifold which later becomes inner channel 18 when sleeve 1 is pulled inside out as shown in FIGS. 3–5. By seaming (e.g. stitching, heat sealing, gluing, etc.) along both the outer and inner margins of the bifold, separate channeled casings (16 and 18) for housing the elastic drawstring 14 and the resilient layer 12 are thereby effectively fabricated from sleeve member 3. The manufacture of the protective sleeve 1 may then be completed by seaming together the remaining sleeve edges along the major longitudinal axis of the flat stock to form the tubular sleeve followed by turning the seamed sleeve inside out to provide the desired protective sleeve 1 having the stitched or heat-sealed seams internally disposed within the sleeve chamber 5. Placing the stitched seam within chamber 5 is done primarily for aesthetic purposes. The turning of the seamed sleeve inside out results in the inside bifold becoming the outside channel casing 16 while the outside bifold becomes the inside channel casing 18. If desired, the sleeve forming margins may be seamed together by stitching, heat sealing, etc., without turning the seamed sleeve inside out while maintaining the drawstrings 14 outside and resilient layer 12 inside so as to provide the appropriate orientation. FIG. 6 serves to illustrate the technique whereby the separate casings 16 and 18 may be provided by sleeve member 3 and not necessarily the actual positioning relationship when a stitched sleeve is turned inside out.

The aforementioned manufacture provides an effective method for economically producing protective sleeves 1 utilizing a water-resistant sheet stock as a base material for forming a sleeve member 3 which also provides separate channel encasements 16 and 18 for housing the drawstrings 14 and the resilient layer 12 therewithin. Effective protection and sealing of the medicinal site S from external contamination generally necessitates a uniform sealing effect between the sleeve member 3 and the appendage A, which may be effectively accomplished by applying a uniform sealing pressure through the resilient layer 12 against the sleeve member 3 and the appendage A. Elastic drawstring 14, when stretched at both loose ends, will typically apply a uniform compressive force against the resilient layer 12 provided drawstring 14 moves freely and applies a uniform contractive or stretched force along the entire length of the encased drawstring 14. The adjustable drawstrings 14 of this invention permits the contractive force to be adjusted to accommodate the appendage size. Non-uniformity in a contractive force by drawstring 14 can also arise if the encasing channel 16 within which the elastic drawstring 14 is housed fails to permit the drawstring 14 to freely move within the drawstring channel 16 and especially when upon drawing the drawstring 14 is drawn tautly so as to apply a sealing compressive force upon the resilient layer 12. Freedom of elastic movement when applying the elastic drawstring 14 thus effectuates uniformity in applied pressure to the resilient layer 12 so that layer 12 may uniformly distribute the sealing force evenly about opening 7.

The present invention also provides an effective method for protectively sealing a medicinal site S upon a bodily appendage A from external contamination with a protective sleeve 1 comprised of an elongated waterproof sleeve member 3 for protectively covering the medicinal site, a plurality of laterally disposed elastic sections 10 for sealing the sleeve member 3 onto the appendage A and protecting the medicinal site from wetness with said elastic sections 10 respectively housing a resilient layer 12 circumferentially disposed about a sleeve chamber opening 7 for placing the sleeve 1 at both sleeve ends over the appendage A, a drawstring 14 circumscribing the resilient layer 12 and drawstring ports 15 for drawing the drawstring 14 and sealing said elastic sections 10 against said appendage A, said method comprising a) placing the protective sleeve 1 over the appendage A so as to cover the medicinal site S; and b) sealing the elastic sections 10 onto the appendage A by circumferentially drawing the drawstring 14 onto the resilient layer 12 of each of said elastic sections 10 and thereby conformingly sealing the elastic sections 10 of the protective sleeve 1 to said appendage A.

The protective method of this invention may be applied to any portion of a human body which would permit the sleeve 1 to be slipped over and protectively sealed at the elastic section 10 against the body portion A. The elastic sections 10 may be suitable adjusted to the appropriate size by drawing the drawstrings 14 to the correct tension level and securing the drawstrings 14 at the adjusted level so as to maintain the correct conforming pressure against the resilient layer 12 and sleeve member 3. The procedure may be repeated by removing the sleeve member 3 from the patient by untieing the drawstrings 14 and later resecuring the protective sleeve when applied for reuse or another site S.

It is to be appreciated that while the invention has been described in greater detail in its preferred embodiments, many changes and modifications may be made in the material out of which the flexible waterproof or water-resistant material is made a well as in the draw strings and the material out of which the elasticized sections are made without departing from the spirit and scope of the invention which is defined herewith in the appended claims.

What is claimed is:

1. A protective sleeve useful for placement over a bodily appendage to protect a medicinal site from external contamination, said sleeve comprising an elongated water-resistant sleeve member for protectively covering the site, a plurality of laterally disposed elastic sections for sealing the sleeve member against the appendage and protecting the medicinal site from the external contamination, with each of said elastic sections including a resilient layer circumscribing an internally disposed chamber opening for slipping the sleeve member over the appendage and an elastic drawing means circumferentially disposed about the resilient layer so that the elastic drawing means, when elastically drawn to a contractive position, applies a contractive force against the layer so as to conformingly seal the sleeve member against the appendage.

2. The elongated sleeve of claim 1 wherein the elastic drawing means comprises an elastic band concentrically encompassing the resilient layer.

3. The protective sleeve of claim 2 wherein said resilient layer comprises foam rubber.

4. The protective sleeve according to claim 2 wherein the sleeve includes securing means for securing the elastic band at the contractive position.

5. The protective sleeve according to claim 4 wherein the sleeve member includes an inner channeled casing encasing the resilient layer.

6. The protective sleeve according to claim 5 wherein the resilient layer comprises a foamed rubber layer protectively encased within an inner channeled casing.

7. The protective sleeve according to claim 6 wherein the elastic section comprises two elastic sections laterally disposed at sleeve openings positioned at opposite ends of the sleeve.

8. The protective sleeve according to claim 1 wherein the elastic drawing means comprises an adjustable drawing means equipped with securing means for securing and maintaining the drawing means at the contractive position.

9. The sleeve according to claim 8 wherein the sleeve member serves as a protective housing for separately encasing the elastic drawing means and the resilient layer.

10. The sleeve according to claim 1 wherein the elastic means comprises an elastic drawstring and the sleeve member provides an outer channeled casing for encasing the elastic drawstring.

11. The sleeve according to claim 10 wherein the outer channeled casing includes drawstring ports for threading opposite ends of the drawstring through the ports so as to permit the opposite ends of the drawstrings when elastically drawn to apply the contractive force upon the sleeve member.

12. A method for protectively sealing a medicinal site upon a bodily appendage from wetness with a protective sleeve comprised of an elongated waterproof sleeve member for protectively covering the medicinal site, a plurality of laterally disposed elastic sections for placing the sleeve over the appendage and conformingly sealing the protective sleeve onto the appendage so as to protect the medicinal site from wetness with said elastic sections respectively housing a resilient layer disposed about an internally disposed chamber opening, elastic drawing means for applying a contractive force upon the resilient layer when the elastic drawing means are drawn to the contractive position so as to seal said elastic sections against said appendage, said method comprising:

a) placing the protective sleeve over the appendage so as to cover the medicinal site; and b) sealing the elastic sections onto the appendage by elastically drawing the drawing means to the contractive position so as to conformingly seal the elastic sections of the protective sleeve against said appendage.

13. The process of claim 12 wherein the elastic means comprises an elastic drawstring and the method includes stretching the elastic drawstring to the contractive position so as to conformingly seal of the sleeve member against the appendage.

14. The method of claim 12 wherein said resilient layer comprises a foam rubber layer and the stretching of the drawstring causes the foam rubber layer to compressively conform about said appendage.

15. The method according to claim 14 which method includes an additional step of securing the drawstring at the contractive position so as to maintain a constant contractive force by said drawstring upon said layer.

16. The method according to claim 12 wherein the resilient layer comprises a foamed rubber layer circumscribing the chamber opening and the drawing means comprises elastic drawstrings concentrically positioned about the layer with terminal segments of the drawstring at opposite ends of the drawstrings protruding from drawstring ports so as to permit an application of the contractive force by pulling the opposite ends in opposing directions and the method includes stretching the drawstring at each of said elastic sections by the pulling of the opposite ends in opposite directions to apply the contractive force and thereafter securing of the opposite ends together so as to maintain the contractive force upon said foamed rubber layer.

17. The method according to claim 16 which includes an additional step of exposing the appendage fitted with the protective sleeve to bathing and thereafter removing the protective sleeve from the appendage.

18. A method for manufacturing a protective sleeve useful for placement over a bodily appendage to protect a medicinal site from external contamination wherein the sleeve includes an elongated water-resistant sleeve member for covering the site, a pair of laterally disposed elastic sections for sealing openings at opposite sleeve ends of the sleeve member against the appendage and protecting the medicinal site from the external contamination, with each of said elastic sections including a resilient layer circumscribing an internally disposed sleeve opening for slipping the sleeve member over the appendage, an elastic drawstring circumferentially disposed about the resilient layer so that the drawstring, when drawn, applies a compressive elastic force against the layer to conformingly seal the sleeve member against the appendage, with said drawstring and said resilient layer being separately encased within said sleeve member and separated by said sleeve member, said method comprising:

a) patterning the sleeve member from a sheet of water-resistant material;

b) bifolding the sleeve member at the sleeve opening to provide an accordion bifold having an outer pleated channel for receiving the drawstring therewithin and an inner pleated channel for housing the resilient layer therewithin;

c) inserting the drawstring within the outer channel and the resilient layer within the inner channel; and d) separately encasing said drawstring within said outer channel of said sleeve member and said resilient layer within said inner channel.

19. The method according to claim 18 which includes porting the outer channel with laterally disposed ports for threading opposing ends of the drawstring therethrough and thereby threading said opposing ends of the drawstring through said ports.

20. The method according to claim 19 which includes shaping the sleeve member into a tubular sleeve shape.

* * * * *